US009974560B2

(12) United States Patent
Alhumaid

(10) Patent No.: US 9,974,560 B2
(45) Date of Patent: *May 22, 2018

(54) METHOD FOR PUNCTURING THE PERICARDIAL MEMBRANE BY SYNCHRONIZING NEEDLE ADVANCEMENT WITH CARDIAC MUSCLE MOTION

(71) Applicant: Fawaz Alhumaid, Lake Oswego, OR (US)

(72) Inventor: Fawaz Alhumaid, Lake Oswego, OR (US)

( * ) Notice: Subject to any disclaimer, the term of this patent is extended or adjusted under 35 U.S.C. 154(b) by 830 days.

This patent is subject to a terminal disclaimer.

(21) Appl. No.: 14/450,389

(22) Filed: Aug. 4, 2014

(65) Prior Publication Data

US 2014/0343417 A1 Nov. 20, 2014

Related U.S. Application Data

(63) Continuation of application No. 13/625,498, filed on Sep. 24, 2012, now Pat. No. 8,834,506.

(51) Int. Cl.
*A61B 17/34* (2006.01)
*A61B 18/20* (2006.01)
(Continued)

(52) U.S. Cl.
CPC ...... *A61B 17/3403* (2013.01); *A61B 17/3478* (2013.01); *A61B 18/1477* (2013.01); *A61M 5/007* (2013.01); *A61B 6/12* (2013.01); *A61B 18/20* (2013.01); *A61B 18/24* (2013.01); *A61B 2017/00048* (2013.01); *A61B 2017/00703* (2013.01); *A61B 2018/00642* (2013.01); *A61B 2018/00839* (2013.01);
(Continued)

(58) Field of Classification Search
CPC . A61B 17/3478; A61B 17/3403; A61B 18/20; A61B 18/1477; A61B 2017/00703; A61B 18/24; A61B 2018/2005; A61B 18/00642; A61B 2017/00048; A61B 2018/00839; A61B 6/12; A61M 5/007; A61M 2205/3303; A61M 2210/122
See application file for complete search history.

(56) References Cited

U.S. PATENT DOCUMENTS

| | | |
|---|---|---|
| 4,991,578 A | 2/1991 | Cohen |
| 6,442,415 B1 | 8/2002 | Bis et al. |

(Continued)

OTHER PUBLICATIONS

Svendsen, et al., "A Transatrial Pericardial Access: Lead Placement as Proof of Concept," Oct. 23, 2009, American Journal of Physiology—Heart and Circulatory Physiology 298:H287-H293, 2010.

*Primary Examiner* — Theodore Stigell
(74) *Attorney, Agent, or Firm* — Oblon, McClelland, Maier & Neustadt, L.L.P.

(57) ABSTRACT

A method for puncturing a pericardial membrane of a human patient, the method comprising inserting a needle into the chest of the human patient, detecting a phase of a mechanical activity of the heart of the human patient, advancing the needle toward the heart of the human patient in synchronization with the detected phase of the mechanical activity of the heart of the human patient, and repeating the detecting and advancing steps until the pericardial membrane of the human patient is punctured.

12 Claims, 9 Drawing Sheets

(51) Int. Cl.
  *A61B 18/14*   (2006.01)
  *A61M 5/00*   (2006.01)
  *A61B 6/12*   (2006.01)
  *A61B 18/24*   (2006.01)
  *A61B 17/00*   (2006.01)
  *A61B 18/00*   (2006.01)

(52) U.S. Cl.
  CPC ........... *A61B 2018/2005* (2013.01); *A61M 2205/3303* (2013.01); *A61M 2210/122* (2013.01)

(56) References Cited

U.S. PATENT DOCUMENTS

| | | |
|---|---|---|
| 6,666,844 B1 | 12/2003 | Igo et al. |
| 6,692,458 B2 | 2/2004 | Forman et al. |
| 8,308,720 B2* | 11/2012 | Davies ............... A61B 18/1492 606/34 |
| 8,834,506 B2* | 9/2014 | Alhumaid .......... A61B 17/3478 604/506 |
| 2008/0275295 A1 | 11/2008 | Gertner |
| 2012/0095434 A1 | 4/2012 | Fung et al. |

* cited by examiner

METHOD FOR PUNCTURING THE PERICARDIAL MEMBRANE BY SYNCHRONIZING NEEDLE ADVANCEMENT WITH CARDIAC MUSCLE MOTION

CROSS REFERENCE TO RELATED APPLICATIONS

This application is a continuation of U.S. Ser. No. 13/625,498, filed Sep. 24, 2012, now U.S. Pat. No. 8,834,506, which contains subject matter related to that described in commonly owned U.S. patent application Ser. No. 13/943,542, titled "A Pericardial Needle for Physically Separating and Penetrating Pericardial Heart Tissue", inventor "Fawaz Alhumaid", and incorporated herein by reference in its entirety.

The present application contains subject matter related to that described in commonly owned U.S. patent application Ser. No. 14/224,245, now U.S. Pat. No. 9,517,102, titled "A Pericardial Needle for Cauterally Separating and Penetrating Pericardial Heart Tissue", inventor "Fawaz Alhumaid", and incorporated herein by reference in its entirety.

GRANT OF NON-EXCLUSIVE RIGHT

This application was prepared with financial support from the Saudi Arabian Cultural Mission, and in consideration therefore the present inventor has granted The Kingdom of Saudi Arabia a non-exclusive right to practice the present invention.

BACKGROUND

Field of the Disclosure

This invention relates to a method for puncturing the pericardial membrane. More specifically, this invention relates to a method for puncturing the pericardial membrane by synchronizing needle advancement with cardiac muscle motion.

Description of the Related Art

The "background" description provided herein is for the purpose of generally presenting the context of the disclosure. Work of the presently named inventor, to the extent it is described in this background section, as well as aspects of the description which may not otherwise qualify as prior art at the time of filing, are neither expressly nor impliedly admitted as prior art against the present invention.

As cardiac medical care advances, there is an increasing number of therapeutic procedures that require access into the pericardial space. Examples of such procedures are those needed for pacemakers, defibrillators, and ablation of certain arrhythmias. The pericardial space is a virtual space between the outside of the heart muscle and a thin layer of tissue that encases the heart muscle, called the parietal pericardium. The pericardial space contains a small amount of fluid, called the pericardial fluid.

The pericardial fluid is in constant contact with the heart muscle and the coronary arteries, and therefore, may be used to deliver drugs to the heart muscle and/or the coronary arteries. Since the pericardial fluid is of relatively low volume, such method of drug delivery requires a relatively lower dose of drug.

Additionally, the pericardial fluid may be used to introduce an agent into the pericardial space, while localizing the agent to the area around the heart muscle. Such agent is contained within the pericardial fluid, without contaminating other tissue or parts. Also, due to the low turn over rate of the pericardial fluid, such agent is sustained over a relatively long period of time.

Conventionally, and as shown in FIGS. 1A-1C, there are two commonly accepted locations on the chest that may be used for the insertion of the needle 107 to access the pericardial space 105: subxiphoid (FIGS. 1A and 1C) and apical (FIG. 1B). Although the apical location corresponds to a lower risk of damaging extracardiac structures, as not many exist in the needle's path, it is generally avoided due to the presence of a major coronary artery (the Left Anterior Decending coronary artery) in the area where the puncture occurs, and hence the associated risk of puncturing that artery and causing a heart attack. Access into the pericardial space 105 is attained with a blunt tip needle 107 adopted from the field of anesthesia, called the Tuohy needle. The Tuohy needle is an epidural introducer needle. To use the subxiphoid location to access the pericardial space 105 between the heart muscle 101 and the parietal pericardium 103, the needle 107 is carefully inserted between the Xiphoid process 109 and the diaphragm 111, and advanced toward the heart muscle 101 in order to penetrate the parietal pericardium 103 without damaging or penetrating the heart muscle 101.

Multiple advancements of the needle, with gradual increase in pressure applied to the parietal pericardium 103 may be required until it is punctured. In order to determine if/when the parietal pericardium 107 is punctured, test injections of a contrast agent may be done following each advancement. Once the parietal pericardium 107 is punctured, the contrast agent can be seen filling the pericardial space 105. At this point, no additional punctures are done.

With the exception of patients with a pericardial effusion (a large amount of fluid collection in the pericardial space due to bleeding or other disease process), the process of accessing the pericardial space 105 is a difficult one with a relatively high complication rate due to the small space between the parietal pericardium 103 and the heart muscle 101 (few millimeters at most) and the continuous motion of the heart before, during, and after puncturing the parietal pericardium 107.

In some cases, the needle tip may penetrate the heart muscle 101, creating a leak of blood from the inside of the heart into the pericardial space 105. Such leak can lead to tamponade and hypotension. In other cases, the needle tip may damage a coronary artery (arteries that supply the heart muscle with oxygen and nutrients), which can cause a heart attack. Such complications are life-threatening if not quickly and properly addressed.

Other possible risks include damage to extracardiac structures that are present in the needle's path. For example, the needle may puncture the stomach, colon, liver, or diaphragm. It may also lacerate an artery causing significant bleeding. Such complications are serious, and potentially life-threatening.

SUMMARY

This disclosure relates to a method for puncturing a pericardial membrane.

In one aspect of the invention, there is provided a method that includes puncturing a pericardial membrane by synchronizing needle advancement with cardiac muscle motion, minimizing the potential for damage to the heart muscle.

In one aspect of the invention, there is provided a method without invasive surgery that includes puncturing a pericardial membrane by synchronizing needle advance with cardiac muscle motion, while avoiding the damaging of the heart muscle.

In another aspect of the invention, there is provided a method that includes puncturing a pericardial membrane by synchronizing needle advance with the cardiac systolic motion, while avoiding the damaging of the heart muscle.

In another aspect of the invention, there is provided a method that includes puncturing a pericardial membrane by synchronizing needle advancement with the movement of the heart based on a phase of an electrocardiogram, while avoiding the damaging of the heart muscle.

In another aspect of the invention, there is provided a method that includes puncturing a pericardial membrane by synchronizing needle advancement with the movement of the heart based on the detection of a QRS complex within an electrocardiogram, while avoiding the damaging of the heart muscle.

In another aspect of the invention, there is provided a method that includes puncturing a pericardial membrane by synchronizing needle advancement with the movement of the heart based on a pressure detected at the tip of a needle used for puncturing the pericardial membrane, while avoiding the damaging of the heart muscle.

In another aspect of the invention, there is provided a method that includes puncturing a pericardial membrane by synchronizing needle advancement with the movement of the heart based on an arterial pressure measurement, while avoiding the damaging of the heart muscle.

In another aspect of the invention, there is provided a method that includes puncturing a pericardial membrane by, for example, a physical, cautery, radio frequency, or a laser needle, by synchronizing needle advancement with the movement of the heart, while avoiding the damaging of the heart muscle.

In another aspect of the invention, there is provided a method that includes puncturing a pericardial membrane by synchronizing needle advancement with the movement of the heart, while avoiding the damaging of the heart muscle, and monitoring a contrast agent injected via a needle used for puncturing the pericardial membrane to detect when the pericardial membrane is punctured.

The disclosed methods make accessing the pericardial space easier and safer by utilizing the cardiac motion to puncture the parietal pericardium in synchronization with that motion.

The disclosed methods may be used to access the pericardial space in order to deliver drugs to the heart muscle and/or the coronary arteries. Since the pericardial fluid is of relatively low volume, delivering drugs via the pericardial fluid requires a relatively lower dose of drug.

The disclosed methods may be used to access the pericardial space in order to introduce an agent into the pericardial space, thereby localizing the agent to the area around the heart muscle. Such agent is thereby contained within the pericardial fluid, without contaminating other tissue and/or space. Also, due to the low turn over rate of the pericardial fluid, such agent is sustained over a longer period of time.

The disclosed methods may be used to access the pericardial space in order to insert a catheter to deliver drugs and/or agents.

The disclosed methods may be used to access the pericardial space in order to insert a catheter to collect biological tissue or cells.

The disclosed methods may be used to access the pericardial space in order to insert a catheter into a specific area of the heart to perform ablation of arrhythmia. Ablation of arrhythmia is performed by directing energy through a catheter to small areas of the heart muscle that cause or participate in abnormal heart rhythm, to eliminate the source of such abnormal rhythm. This process may also be used to disconnect an abnormal electrical pathway between the atria and the ventricles.

The disclosed methods may be used to access the pericardial space in order to insert a catheter or tool to ligate the left atrial appendage.

The disclosed methods may be used to access the pericardial space, in situations where a cardiac procedure has led to bleeding into the pericardial space, to insert a catheter to drain blood from the pericardial space until the bleeding source seals on its own, or until a surgical procedure is done to repair it.

The disclosed methods may be used to access the pericardial space, in situations where a disease process has led to the accumulation of blood or other types of fluid in the pericardial space, to insert a catheter to drain this fluid for diagnostic purposes, and/or to relieve the pressure exerted on the heart and improve its function.

The disclosed methods may be used to access the pericardial space, in order to introduce implantable defibrillator and/or pacemaker electrodes into the pericardial space.

The disclosed methods may be used under fluoroscopy guidance (X Ray), ultrasound, or CT scan.

The disclosed methods may also be used under magnetic resonance imaging when a non-metal needle is used.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1A:
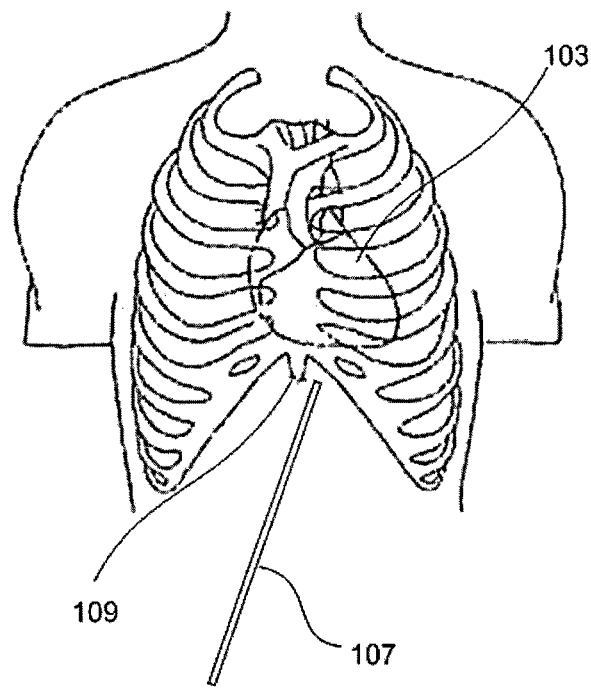
FIGS. 1A-1C are illustrations of methods of accessing the pericardial space.
Figure 1B:
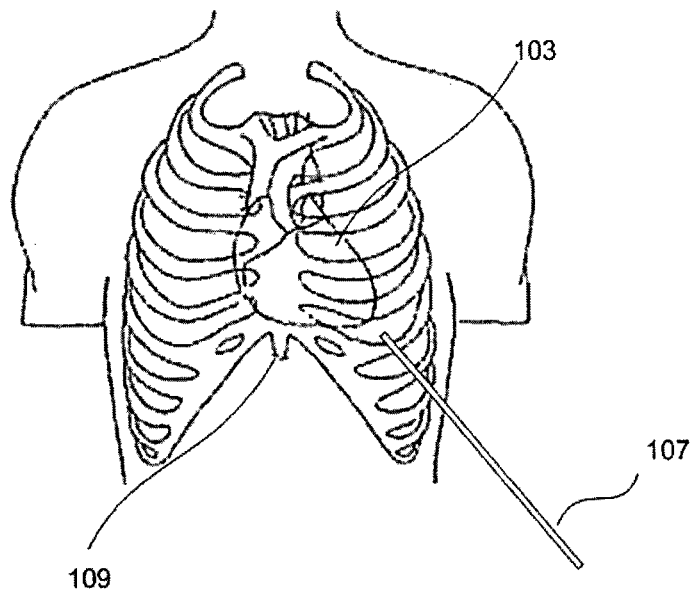
Figure 1C:
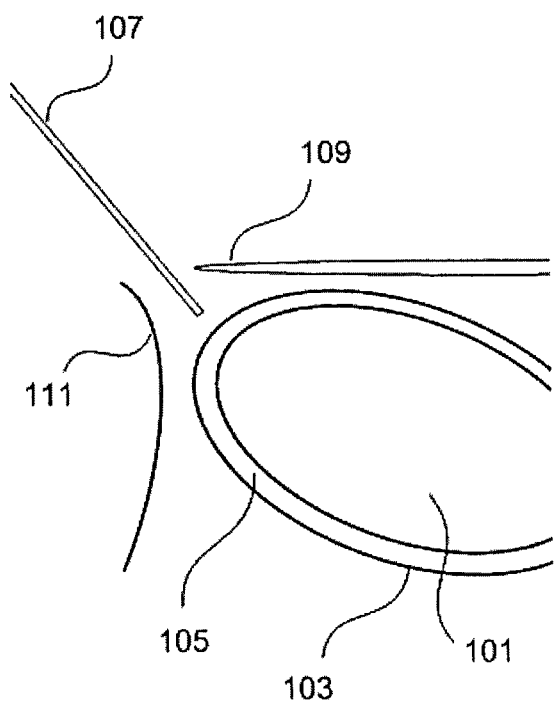
Figure 2A:
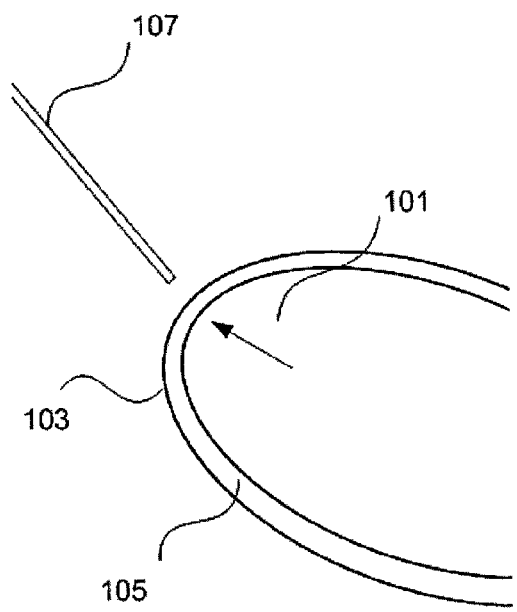
FIGS. 2A and 2B are illustrative views of a process of accessing the pericardial space when the heart is in systole and diastole, respectively.
Figure 2B:
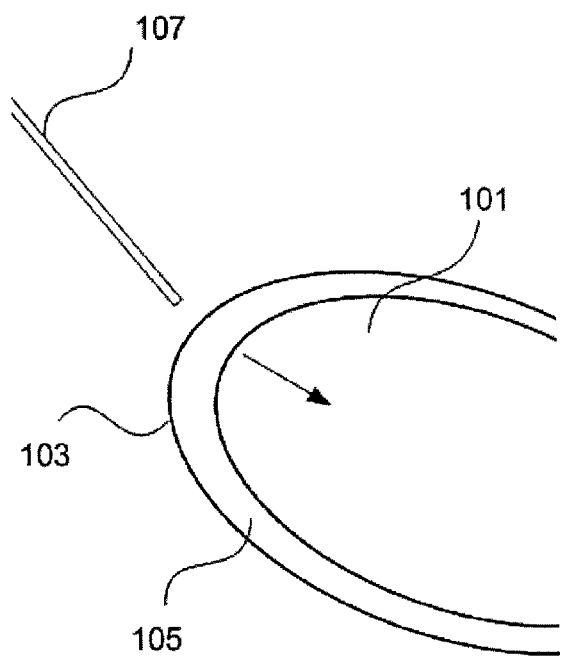

Referring now to the drawings, wherein like reference numerals designate identical or corresponding parts throughout the several views, FIGS. 2A and 2B are illustrative views of a process of accessing the pericardial space 105 when the heart is in systole and diastole, respectively. The heart muscle 101 is in continuous motion. This motion is periodic and is called the cardiac cycle. The cardiac cycle is composed of two main phases called systole and diastole. Systole is the phase where the ventricles contract, causing the heart to eject blood out of its inner cavities. Diastole is the relaxation phase during which the ventricles relax and fill with blood.

As the needle 107 advances towards the pericardial space 105, the motion of the heart muscle 101 (the ventricles) has significant impact on the ability to achieve the goal of penetrating one layer (the parietal pericardium 103), without penetrating or damaging the adjacent moving heart muscle 101.

The inventor of the present disclosure identified that the risk of inadvertently penetrating the heart muscle 101 is significantly lower if the penetration of the parietal pericardium 103 is synchronized with systole. This is due to the fact that the heart muscle 101 is moving away from the needle 107 during systole, and as shown in FIG. 2B. Thus, the disclosed methods of the present disclosure take advantage of the motion of the heart muscle 101, and change this motion from a factor that adds to the risk of the procedure, to one that helps attain safer access to the pericardial space 105.

The parietal pericardium 103 encases the heart muscle 101. The distance between the parietal pericardium 103 and the outer layer of the ventricles (the visceral pericardium) changes slightly as the heart muscle 101 moves. This change in the distance between the parietal pericardium 103 and the ventricles provides a time window of opportunity for safer access to the pericardial space 105, when such access is synchronized with the movement of the heart muscle 101.

According to an embodiment of the present disclosure, accessing the pericardial space 105 may be achieved by advancing through the parietal pericardium 103 in brief pulses, and synchronizing these pulses to systole where the ventricles contract, thereby moving away from the needle 107, relax, thereby moving towards the needle 107, and/or rest and is in a static condition.

According to an embodiment of the present disclosure, accessing the pericardial space 105 may be achieved by inserting a needle between the ribs at the left side of the chest. Even though important coronary arteries may exists in such location, the associated risk of inadvertently puncturing a coronary artery is reduced due to the synchronization of the needle advancement with the movement of the heart muscle 101, thereby making this location a viable option to be used in the process of accessing the pericardial space 105.

In order to detect and synchronize with systole, visual, mechanical, electrical, or any other measurement indicative and/or predictive of systole, diastole and/or the heart condition may be utilized.

According to an embodiment of the present disclosure, an echocardiogram may be used by a physician performing the process, to visually monitor the motion of the cardiac muscle.

Figure 3:
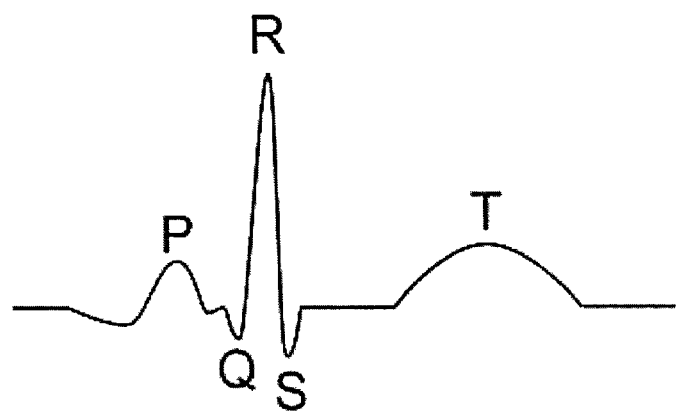
FIG. 3 is a graph of an electrocardiogram.

According to another embodiment of the present disclosure, an electrocardiogram (ECG) may be utilized to indicate the phase of the cardiac cycle, and synchronize with systole. FIG. 3 is a graph of an ECG. ECG is a recording of the electrical activity of the heart. A typical ECG of the cardiac cycle (one heartbeat) consists of a P-wave, a QRS complex, and a T-wave. The P-wave reflects the atrial activation. The QRS complex reflects the ventricular activation, which is the electrical activity that causes the ventricular heart muscle to contract. Accordingly, the actual systolic mechanical motion of the ventricles shortly follows the onset of the QRS complex shown in the ECG in FIG. 3.

Typically, mechanical systole starts approximately 30-40 milliseconds after the onset of the QRS waveform (e.g., beginning of the Q wave), and lasts for approximately 300-350 milliseconds at resting heart rate in normal hearts. The duration of systole and the time between the onset of the QRS waveform and the beginning of systole may be altered by the heart rate, age, gender, body mass index (BMI), and/or the presence and nature of underlying heart disease in a human patient.

According to an embodiment of the present disclosure, the needle 107 may be advanced preferably any time after the beginning and before the end of systole. According to an embodiment, the needle 107 may be advanced in a time window of 310 milliseconds, starting at 40 milliseconds after the onset of the QRS waveform and ending at 350 milliseconds after the onset of the QRS waveform.

According to another embodiment of the present disclosure, the time window allowed for needle advancement may be adjusted based on one or more of many contributing factors including the heart rate, age, gender, and BMI of a human patient, in addition to the presence and nature of underlying heart disease. Such adjustment may be in terms of a percentage of the time window. Such adjustment may be manually performed by the physician performing the process of puncturing the parietal pericardium 103, or may be automatically performed by a controller. Lab testing may be used to search for the best time interval during the cardiac cycle and/or during systole.

Figure 4:
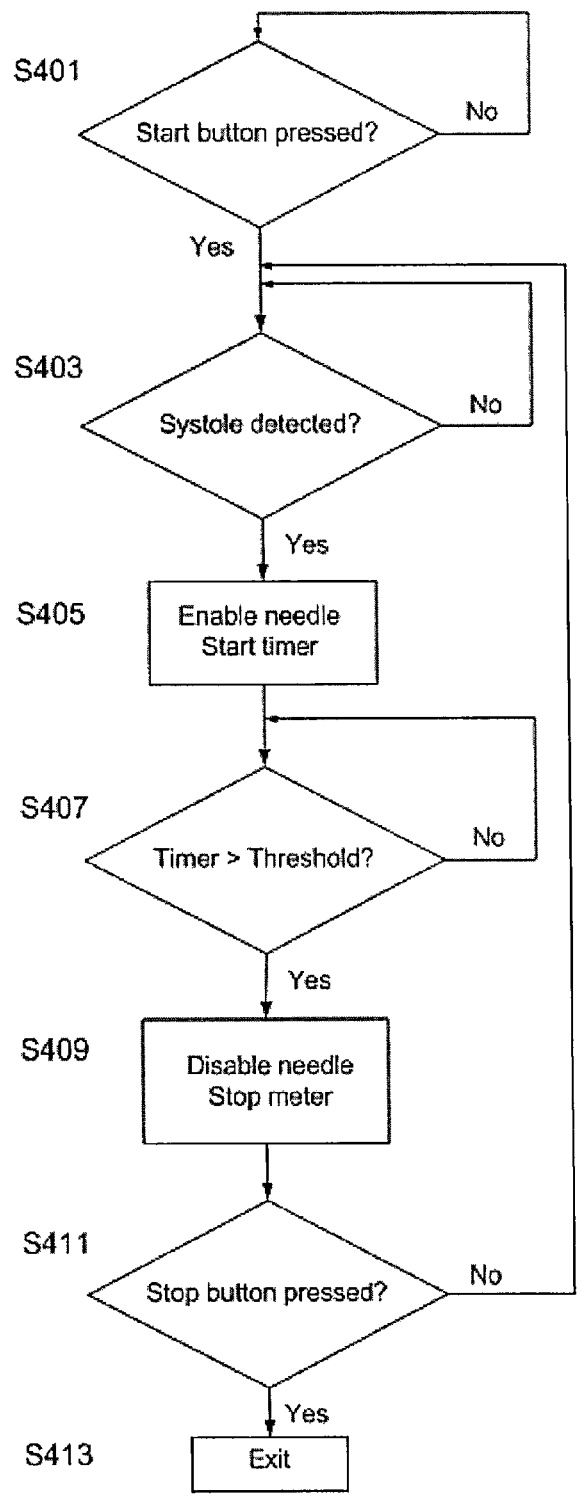
FIG. 4 is a flowchart for an embodiment of a method of synchronizing the process of accessing the pericardial space with the heart's systole.

FIG. 4 is a flowchart for an embodiment of a method of synchronizing the process of accessing the pericardial space 105 with the heart's systole.

In step S401, the process determines whether an instruction for initiation of the process has been given. For example, a start button may be pressed by a physician, indicating the initiation of the process of accessing the pericardial space 105. If no indication of initiation has been detected, the process loops back to step S401. Otherwise, the process proceeds to step S403.

In step S403, the process checks if systole is detected. Detection of systole may be according to visual, mechanical, electrical, or any other measurement indicative of systole. If systole is not detected, the process loops back to step S403. Otherwise, the process proceeds to step S405.

In step S405, the needle 107 is enabled and a timer is started.

According to an embodiment, a cautery needle, previously held in a disabled state, may be enabled in step S405, such that the cautery needle punctures the parietal pericardium 103 when cautery is enabled.

According to another embodiment, a needle blade, previously held in a secured state, may be released in step S405, such that the needle blade punctures the parietal pericardium 103 when released.

According to another embodiment, a laser needle, previously held in an inactive state, may be activated in step S405, such that the laser needle punctures the parietal pericardium 103 when activated.

In step S407, the process checks if the timer has exceeded a predetermined threshold. The predetermined threshold may be set according to an estimate of the duration of systole. If the timer has not exceeded a predetermined threshold, the process loops back to step S407. Otherwise, the process proceeds to step S409.

In step S409, the needle 107 is disabled and the timer is stopped.

According to an embodiment, a cautery needle is disabled in step S409, such that cautery is no longer deliverable, so that the needle does not punctures the parietal pericardium 103 when disabled.

According to another embodiment, a needle blade is secured in step S409, such that the needle blade does not puncture the parietal pericardium 103 when secured.

According to another embodiment, a laser needle is de-activated in step S409, such that the laser needle does not puncture the parietal pericardium 103 when de-activated.

In step S411, the process checks if an instruction to stop needle advancement and/or stop the process has been received. For example, a stop button may be pressed by a physician, indicating the success and/or termination of the process of accessing the pericardial space 105. If the process has not been interrupted, the process loops back to step S403. Otherwise, the process exits in step S413.

Multiple advancement toward the parietal pericardium 103 may be needed in order to successfully puncture the pericardial membrane. A physician may determine the success of puncturing the parietal pericardium 103 by monitoring the operation and looking for the indication that a test contrast agent injection flows into the pericardial space 105 as observed under fluoroscopy imaging.

Figure 5:
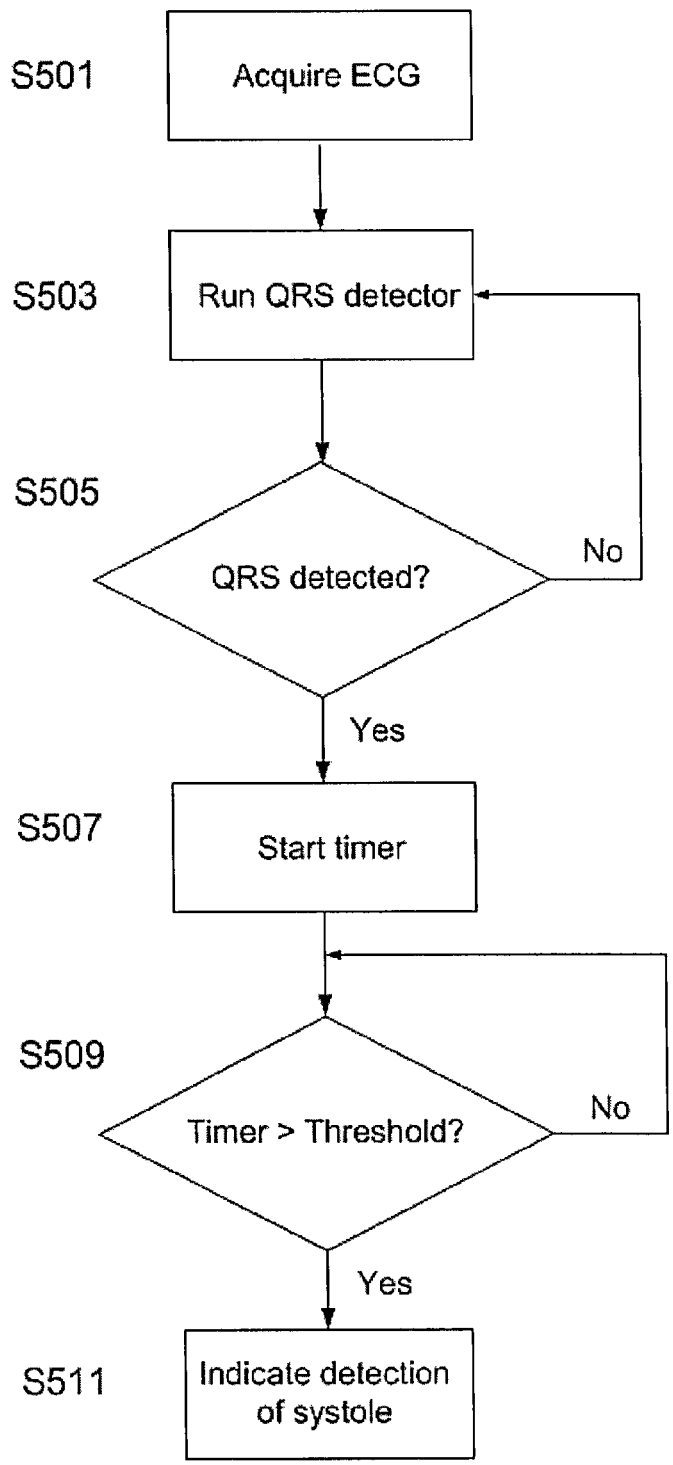
FIG. 5 is a flowchart for an embodiment of a method of detecting systole based on an electrocardiogram.

As previously mentioned, detection of systole may be according to visual, mechanical, electrical, or any other measurement indicative of systole. FIG. 5 is a flowchart for an embodiment of a method of detecting systole based on the ECG.

In step S501, ECG is acquired.

According to an embodiment, acquisition of ECG may be according to a conventional method via ECG electrodes, followed by ECG instrumentation and signal processing.

According to another embodiment, acquisition of ECG may be according to conventional ECG electrodes, followed by ECG instrumentation and signal processing, and wireless transmission of the ECG signals to a controller.

According to an embodiment, acquisition of ECG may be according to conventional ECG electrodes, followed by ECG instrumentation and signal processing, and fiber optic transmission of the ECG signals to a controller.

In step S503, a QRS detector is run.

According to an embodiment, detection of QRS may be according to a conventional method of slope detection.

According to another embodiment, detection of QRS may be according to an envelope or template detection. The envelope or template detection may be according to a previously acquired QRS, or according to a standard QRS profile or template. The standard QRS profile or template may be adjustable according to one or more of an age, gender, BMI, heart rate, or the presence and nature of an underlying heart disease in a human patient.

According to another embodiment, detection of QRS may be according to an extremum detection, such as an R-wave peak detection, a Q-wave minimum detection, or an S-wave minimum detection. Alternatively, detection of QRS may include detection of a sequence of extremums, e.g., a Q-wave minimum followed by an R-wave peak, or an R-wave peak followed by an S-wave minimum.

Detection of QRS may be performed in real-time, and with tolerable delay, such that the detected QRS corresponds to the mechanical activity of the heart in real-time. The tolerable delay between the onset of the QRS complex and the detection of the QRS complex may depend on the duration of systole, and/or the time period between the onset of the QRS complex and systole.

In step S505, the process checks if QRS is detected. If QRS is not detected, the process loops back to step S505. Otherwise, the process proceeds to step S507.

In step S507, a timer is started to measure the time elapsed since the detection of QRS.

In step S509, the process checks if the timer has exceeded a predetermined threshold. The predetermined threshold may be set according to an estimate of the duration of time between the detection of QRS and systole. If the timer has not exceeded the predetermined threshold, the process loops back to step S509. Otherwise, the process proceeds to step S511.

According to an embodiment, the predetermined threshold may be adjustable according to one or more of an age, gender, BMI, presence of underlying heart disease, or heart rate of a human patient.

In step S511, detection of systole is indicated.

Alternatively, other methods may be used to indicate systole.

According to an embodiment of the present disclosure, a pressure measurement may be used to synchronize the process of accessing the pericardial space with systole. The pressure measurement may be performed at the tip of the needle 107. Alternatively, arterial pressure wave, through an arterial line, or pulse oximetry (plethysmographic) waveform may be used.

The arterial blood pressure indicative of systole may be determined by the measurement of the arterial blood pressure before the process of puncturing the parietal pericardium 103, and adjusting the expected arterial blood pressure during systole either manually or automatically. As the arterial blood pressure is subject to variation, such measurement may be updated continually or from time to time, during the process of puncturing the parietal pericardium 103.

Figure 6:
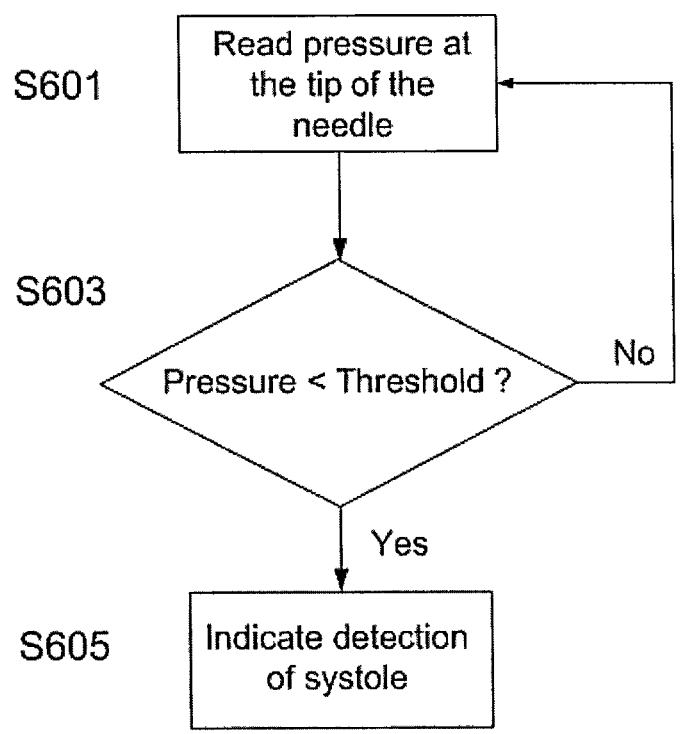
FIG. 6 is a flowchart for an embodiment of a method of detecting systole based on a pressure measurement at the tip of a needle.

FIG. 6 is a flowchart for an embodiment of a method of detecting systole based on a pressure measurement at the tip of the needle 107.

In step S601, a pressure measurement is made at the tip of the needle 107.

In step S603, the process checks if pressure has fallen below a predetermined threshold. The predetermined threshold may be set according to an estimate of the pressure expected at the tip of the needle 107 during systole. If the pressure has not fallen below the predetermined threshold, the process loops back to step S603. Otherwise, the process proceeds to step S605.

According to an embodiment, the predetermined threshold may be adjustable according to one or more of an age, gender, BMI, presence of underlying heart disease, or heart rate of a human patient.

In step S605, detection of systole is indicated.

Figure 7:
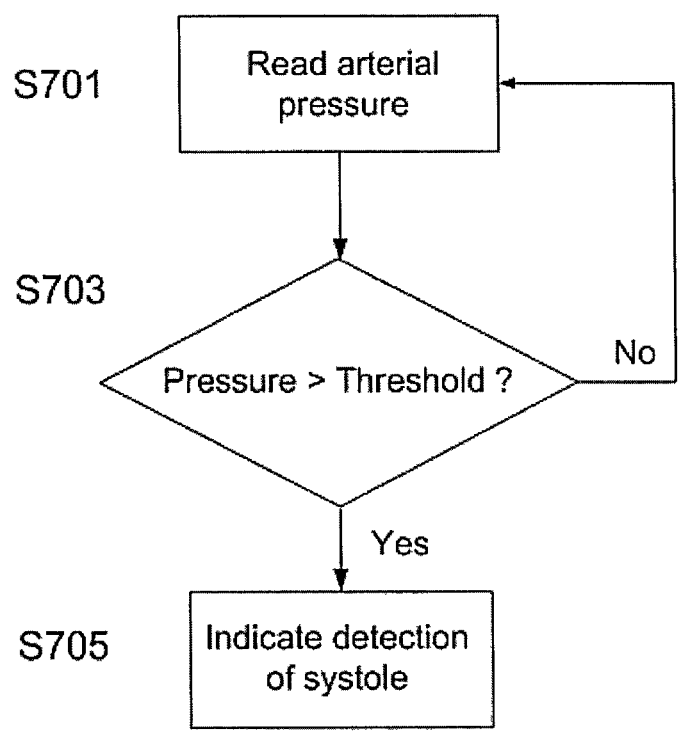
FIG. 7 is a flowchart for an embodiment of a method of detecting systole based on arterial pressure measurement.

FIG. 7 is a flowchart for an embodiment of a method of detecting systole based on arterial pressure measurement.

In step S701, an arterial pressure wave is detected. The detection of the arterial pressure wave may be through an arterial line, or pulse oximetry waveform may be used.

In step S703, the process checks if the arterial pressure has exceeded a predetermined threshold. The predetermined threshold may be set according to an estimate of the arterial pressure during systole. If the arterial pressure has not exceeded a predetermined threshold, the process loops back to step S703. Otherwise, the process proceeds to step S705.

The predetermined threshold may be adjustable according to one or more of an age, gender, BMI, presence of underlying heart disease, or heart rate of a human patient.

In step S705, detection of systole is indicated.

Figure 8:
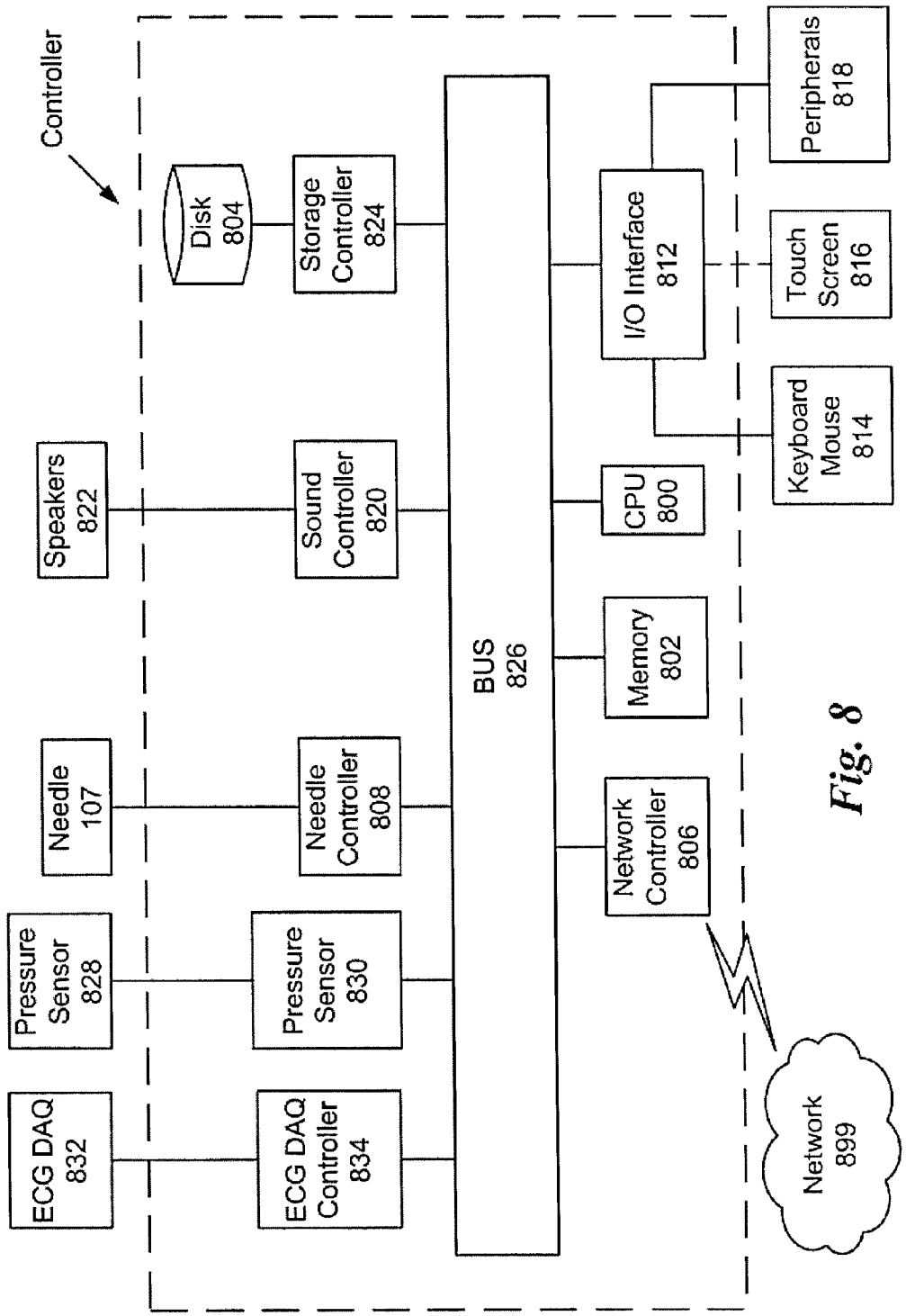
FIG. 8 is a block diagram of a controller.

FIG. 8 is a block diagram of a controller which may be used to perform the above-described processes. A hardware description of the controller according to exemplary embodiments is described with reference to FIG. 8. In FIG. 8, the controller includes a CPU 800 which may be used to perform the processes described in the present disclosure. The process data and instructions corresponding to the processes described in the present disclosure may be stored in memory 802. These processes and instructions may also be stored on a storage medium disk 804 such as a hard drive (HDD) or portable storage medium or may be stored remotely.

Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the controller communicates, such as a server or computer.

Further, the claimed advancements may be provided as a utility application, background daemon, or component of an operating system, or combination thereof, executing in conjunction with CPU 800 and an operating system such as Microsoft Windows 7, UNIX, Solaris, LINUX, Apple MAC-OS and other systems known to those skilled in the art.

CPU 800 may be a Xenon or Core processor from Intel of America or an Opteron processor from AMD of America, or may be other processor types that would be recognized by one of ordinary skill in the art. Alternatively, the CPU 800 may be implemented on an FPGA, ASIC, PLD or using discrete logic circuits, as one of ordinary skill in the art would recognize. Further, CPU 800 may be implemented as multiple processors cooperatively working in parallel to perform the instructions of the inventive processes described in the present disclosure.

The controller in FIG. 8 also includes a network controller 806, such as an Intel Ethernet PRO network interface card from Intel Corporation of America, for interfacing with network 899. As can be appreciated, the network 899 can be a public network, such as the Internet, or a private network such as an LAN or WAN network, or any combination thereof and can also include PSTN or ISDN sub-networks. The network 899 can also be wired, such as an Ethernet network, or can be wireless such as a cellular network including EDGE, 3G and 4G wireless cellular systems. The wireless network can also be WiFi, Bluetooth, or any other wireless form of communication that is known.

The controller further includes a display controller 808, such as a NVIDIA GeForce GTX or Quadro graphics adaptor from NVIDIA Corporation of America for interfacing with display 810, such as a Hewlett Packard HPL2445w LCD monitor. A general purpose I/O interface 812 interfaces with a keyboard and/or mouse 814 as well as a touch screen panel 816 on or separate from display 810. General purpose I/O interface also connects to a variety of peripherals 818 including printers and scanners, such as an OfficeJet or DeskJet from Hewlett Packard.

A sound controller 820 is also provided in the controller, such as Sound Blaster X-Fi Titanium from Creative, to interface with speakers/microphone 822 thereby providing sounds and/or music. The speakers/microphone 822 can also be used to accept dictated words as commands for controlling the controller or for providing location and/or property information with respect to the target property.

The general purpose storage controller 824 connects the storage medium disk 804 with communication bus 826, which may be an ISA, EISA, VESA, PCI, or similar, for interconnecting all of the components of the controller. A description of the general features, detail features, and functionality of the display 810, keyboard and/or mouse 814, as well as the display controller 808, storage controller 824, network controller 806, sound controller 820, and general purpose I/O interface 812 is omitted herein for brevity as these features are known.

An ECG data acquisition (DAQ) controller 834 is also provided in the controller, to interface with an ECG DAQ 832, so an ECG measurement may be controlled, displayed and/or recorded via the controller, and used in a process of accessing the pericardial space.

A pressure sensor controller 830 is also provided in the controller, to interface with a pressure sensor 828, so a pressure measurement may be controlled, displayed and/or recorded via the controller. The pressure measurement may be used in a process of accessing the pericardial space 105.

A needle controller 808 is also provided in the controller, to interface with the needle 107, so the needle 107 may be controlled via the controller.

The disclosed methods make accessing the pericardial space easier and safer by utilizing the cardiac motion to puncture the parietal pericardium in synchronization with the cardiac motion.

The disclosed methods make accessing the pericardial space easier and safer by utilizing the cardiac motion to puncture the parietal pericardium in synchronization with that motion.

The disclosed methods may be used to access the pericardial space in order to deliver drugs to the heart muscle and/or the coronary arteries. Since the pericardial fluid is of relatively low volume, delivering drugs via the pericardial fluid requires a relatively lower dose of drug.

The disclosed methods may be used to access the pericardial space in order to introduce an agent into the pericardial space, thereby localizing the agent to the area around the heart muscle. Such agent is thereby contained within the pericardial fluid, without contaminating other tissue and/or space. Also, due to the low turn over rate of the pericardial fluid, such agent is sustained over a longer period of time.

The disclosed methods may be used to access the pericardial space in order to insert a catheter to deliver drugs and/or agents.

The disclosed methods may be used to access the pericardial space in order to insert a catheter to collect biological tissue or cells.

The disclosed methods may be used to access the pericardial space in order to insert a catheter into a specific area of the heart to perform ablation of arrhythmia. Ablation of arrhythmia is performed by directing energy through a catheter to small areas of the heart muscle that cause abnormal heart rhythm, to disconnect the source of the abnormal rhythm from the rest of the heart. This process may also be used to disconnect an abnormal electrical pathway between the atria and the ventricles.

The disclosed methods may be used to access the pericardial space in order to insert a catheter or tool to ligate the left atrial appendage.

The disclosed methods may be used to access the pericardial space, in situations where a cardiac procedure has led to bleeding into the pericardial space to occur, to insert a catheter to drain blood from the pericardial space until the bleeding source seals on its own, or until a surgical procedure is done to repair it.

The disclosed methods may be used to access the pericardial space, in situations where a disease process has led to the accumulation of blood or other types of fluid in the pericardial space, to insert a catheter to drain this fluid for diagnostic purposes, and/or relieve the pressure exerted on the heart and improve its function.

The disclosed methods may be used to access the pericardial space, in order to introduce implantable defibrillator and/or pacemaker electrodes into the pericardial space.

The disclosed methods may be used under fluoroscopy guidance (X Ray), ultrasound, or CT scan.

The disclosed methods may also be used under magnetic resonance imaging when a non-metal needle is used.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, define, in part, the scope of the foregoing claim terminology such that no inventive subject matter is dedicated to the public.

The invention claimed is:

1. A method for puncturing a pericardial membrane of a human patient, the method comprising:
    inserting a needle into the chest of the human patient;
    detecting a phase of a mechanical activity of the heart of the human patient;
    advancing the needle toward the heart of the human patient in synchronization with the detected phase of the mechanical activity of the heart of the human patient;
    repeating the detecting and advancing steps until the pericardial membrane of the human patient is detected and the needle is in contact with or proximal the pericardial membrane;
    puncturing the pericardial membrane of the heart of the human patient with an advancement pulse of the needle, wherein the advancement pulse is synchronized with a QRS complex of the heart monitored by electrocardiography, based on a slope of the electrocardiogram of the human patient corresponding with the QRS complex;
    wherein the advancement pulse of the needle is activated by a controller programmed with instructions to advance a blade of the needle in synchronization with the QRS complex of the heart of the patient.

2. The method of claim 1, wherein the detecting the phase of the mechanical activity of the heart of the human patient is based on an electrocardiogram of the human patient.

3. The method of claim 2, wherein the detecting the phase of the mechanical activity of the heart of the human patient includes:
    monitoring the electrocardiogram of the human patient to identify the phase of the mechanical activity of the heart of the human patient.

4. The method of claim 2, wherein the detecting the phase of the mechanical activity of the heart of the human patient further comprises:
    acquiring the electrocardiogram of the human patient;
    detecting a QRS complex within the electrocardiogram of the human patient;
    waiting for a predetermined time after the detected QRS complex; and
    indicating a systole phase of the heart of the human patient when the predetermined time after the detected QRS complex has elapsed.

5. The method of claim 4, further including:
    adjusting the predetermined time based on at least one of an age, a gender, a heart rate, a presence of an underlying heart disease, or a body mass index of the human patient.

6. The method of claim 4, wherein the detecting the QRS complex within the electrocardiogram of the human patient includes:
    determining a correlation between a time window of the electrocardiogram of the human patient and a predetermined QRS template; and
    determining if the determined correlation has exceeded a predetermined correlation threshold.

7. The method of claim 6, further including:
    determining the predetermined QRS template based on a previously acquired QRS complex of the human patient.

8. The method of claim 1, wherein the detecting the phase of the mechanical activity of the heart of the human patient includes:
    measuring a pressure at the tip of the needle;
    determining if the measured pressure has fallen below a predetermined pressure threshold.

9. The method of claim 8, further including:
    adjusting the predetermined pressure threshold based on at least one of an age, a gender, a heart rate, a presence of an underlying heart disease, or a body mass index of the human patient.

10. The method of claim 1, wherein the detecting the phase of the mechanical activity of the heart of the human patient includes:
    measuring an arterial pressure of the human patient;
    determining if the measured arterial pressure has exceeded a predetermined arterial pressure threshold.

11. The method of claim 10, further including:
    adjusting the predetermined arterial pressure threshold based on at least one of an age, a gender, a heart rate, a presence of an underlying heart disease, or a body mass index of the human patient.

12. The method of claim 1, further comprising:
    injecting a contrast agent from the tip of the needle; and
    determining that the pericardial membrane is punctured when the contrast agent is seen in the pericardial space.

* * * * *